United States Patent [19]
Boulaud et al.

[11] Patent Number: 6,012,343
[45] Date of Patent: Jan. 11, 2000

[54] CHARGED PARTICLE SELECTOR AS A FUNCTION OF PARTICLE ELECTRICAL MOBILITY AND RELAXATION TIME

[75] Inventors: Denis Boulaud, Paris; Michel Pourprix, Montlhery, both of France

[73] Assignee: Commissariat A l'Energie Atomique, Paris, France

[21] Appl. No.: 08/795,795

[22] Filed: Feb. 5, 1997

[30] Foreign Application Priority Data

Feb. 15, 1996 [FR] France ................................ 96-01868

[51] Int. Cl.[7] .......................... G01N 15/14; G01N 15/04
[52] U.S. Cl. .............................................. 73/865.5; 95/34
[58] Field of Search ................................ 73/865.5; 95/34

[56] References Cited

U.S. PATENT DOCUMENTS

| | | | |
|---|---|---|---|
| 4,639,143 | 1/1987 | Prodi | 209/143 |
| 4,657,667 | 4/1987 | Etkin | 209/135 |
| 4,872,972 | 10/1989 | Wakabayashi et al. | 209/143 |
| 5,117,190 | 5/1992 | Pourprix | 324/452 |
| 5,150,036 | 9/1992 | Pourprix | 324/71.4 |
| 5,348,163 | 9/1994 | Tunison, III et al. | 209/135 |
| 5,351,832 | 10/1994 | Abbott et al. | 209/139.1 |
| 5,447,275 | 9/1995 | Goka et al. | 241/5 |
| 5,592,096 | 1/1997 | Pourprix | 324/452 |
| 5,606,112 | 2/1997 | Flagan et al. | 73/28.04 |
| 5,620,100 | 4/1997 | Pourprix | 209/127.1 |
| 5,621,208 | 4/1997 | Pourprix | 250/287 |

FOREIGN PATENT DOCUMENTS 0 685 725 12/1995 European Pat. Off. .
0 685 727 12/1995 European Pat. Off. .

OTHER PUBLICATIONS

J. Aerosol Science, vol. 17, No. 1,pp. 79–86, 1986, M. Barbe–le Borgne, et al., "Experimental Determination of the Dynamic Shape Factor of the Primary Sodium Peroxide Aerosol".

J. Aerosol Science, vol. 23, No. 1 pp. 27–35, 1992, E.P. Emets, et al., "A New Technique for the Determination of the Density Of Airborne Particulate Matter".

Aerosol Science and Technoloy, vol. 23, pp. 155–173, 1995, Susanne V. Hering, et al., "On–Line Determination of Particle Size and Density in the Nanometer Size Range".

J. Aerosol Science, vol. 26, pp. s135–s136, 1995, K. Ehara, et al., "Classification of Aerosol Particles According to Mass–to–Charge Ratio".

*Primary Examiner*—Thomas P. Noland
*Attorney, Agent, or Firm*—Oblon, Spivak, McClelland, Maier & Neustadt, P.C.

[57] ABSTRACT

A charged particle selector having first and second circular electrical mobility selector portions is shown to include directing portions for directing particles selected by the first circular electrical mobility selector to the input of the second circular electrical mobility selector. These selectors may be combined to be in parallel instead of in series. The charged particle selector can be used to make in-line measurement of the mass and/or density of aerosol particles, to make measurements of the size of the particles and/or their distribution as well as the distribution of aerosol electrical charges.

10 Claims, 5 Drawing Sheets

CHARGED PARTICLE SELECTOR AS A FUNCTION OF PARTICLE ELECTRICAL MOBILITY AND RELAXATION TIME

DESCRIPTION

TECHNICAL FIELD AND PRIOR ART

This invention relates to a device for selecting charged particles as a function of their electrical mobility and their relaxation time, and characterizing aerosols in terms of particle masses, particle size and distribution of electrical charges.

For example, this type of equipment is particularly useful for testing the efficiency of filters and for producing calibrated particles, or for studying the electrical charge of aerosols, in the aerosol research field. It is particularly suitable for micronic and/or submicronic aerosols.

There are various techniques for the in line measurement of the size distribution of micronic and/or submicronic aerosols. For example, there are electrical methods, and particularly differential electrical mobility analyzers that provide a size distribution based on the electrical mobility of particles. Optical methods provide a size distribution related to the optical properties of particles. Aerodynamic methods provide a size distribution based on particle inertia.

A limitation to these measurement methods is that they do not make any distinction between different types of particles. Thus this gives the global size distribution, but never the distribution as a function of the nature of the particles. In order to determine the composition and the size, a sampling is usually necessary that will enable a subsequent analysis by electronic or optical microscopy. These procedures are long, expensive and tedious, and do not provide the required information on line.

In particular, one technique for determining the mass and density of aerosol particles consists of starting by taking a sample and collecting a fraction of the aerosol with a clearly defined diameter on a suitable support such as a filter membrane, grill or microscope slide, and secondly carrying out an analysis in order to determine the average mass of each particle. The average mass may be derived from the total mass of the sample taken, and the number of the particles present. This method was described in the article by Barbe-Le Borgne et al. that was published in the "Journal of Aerosol Science", vol. 17, No. 1, pp. 79–86, 1986. The method described in this article is used to characterize particles originating from a sodium fire. This method uses firstly a selection of sizes of a sample, using any appropriate system (impactor, centrifuge, sedimentation bank, electrical mobility analyzer), said sample then being observed with an electronic or optical microscope to count the number of particles present. The sample is then analyzed by the most suitable means to determine the mass and composition (for example by neutronic activation technique, or by X fluorescence or emission spectrometry). It is obvious that this method is long, tedious and expensive. Furthermore, taking a sample at the same time as doing the collection can modify the particle structure.

There are two other known types of devices for determining the density of particles on line.

The first technique is described in the article by E. P. Emets et al. published in the "Journal of Aerosol Science", vol. 23, No. 1, pp. 27–35, 1992. This method uses the combination of two differential electrical mobility analyzers with axial flow, one with its axis vertical and the other with its axis horizontal. Particles are detected using an optical counter on the downstream side of this device. The measurement of the particle density depends on the fact that the transfer function of the differential analyzer when placed horizontally is deformed from the transfer function for the differential analyzer when placed vertically. Under these conditions, counts on the downstream side of a differential analyzer placed horizontally are not the same as counts for the same differential analyzer placed horizontally, for the same aerosol. The particle density can be determined from this count difference, by using an extremely complex mathematical development, particularly to determine the shape of the transfer function of the horizontal differential analyzer. Therefore the interpretation of experimental results is not easy, and can only be done by specialists. This method gives a precision on the density of particles of about 30%.

Another method is described by S. V. Hering et al. in "Aerosol Science and Technology", vol. 23, pp. 155–173, 1995. This method, that the authors refer to as "double size spectrometry", measures the particle size twice. A first measurement is carried out with a differential electrical mobility analyzer that provides the geometric diameter of spherical particles. A second measurement is carried out with a hypersonic impactor and provides information about the particle relaxation time. A comparison of the two measurements gives the particle density, within a range of between 3 and 50 nm. The differential analyzer is now a known and very widely used device, however the hypersonic impactor is a recent instrument, which is difficult to use and is only found in a few laboratories. This impactor works under low pressure and the aerosol relaxation time is measured by determining the impactor transfer function for variable geometric characteristics (particularly variation of the ratio between the size of the critical orifice and the distance separating it from the collection plate). Therefore, this is also a complex system and interpretation of the results is difficult and once again can only be done by specialists. Furthermore, due to its principle, the measurement of the relaxation time or the aerodynamic diameter using a hypersonic impactor operating at low pressure, is only applicable to particles with a size of between 3 and 50 nm.

DESCRIPTION OF THE INVENTION

The invention proposes a new charged particles selector, with a much simpler design than previously known devices, both for the design and operation.

More precisely, the purpose of the invention is a charged particles selector from an atmosphere to be examined, comprising:

a first and a second circular electrical mobility selector, each selector comprising:
first and second coaxial conducting disks, separate and parallel to each other, with an annular inlet slit with radius r1 being formed in the first disk,
a central intake, this intake allowing a laminar, centripetal and stable air flow to circulate in the space between the disks,
means of applying an electrical field between the two conducting disks,
means of directing particles selected by an annular selection slit with radius r2 (r2 <r1) formed in the second disk in the first circular electrical mobility selector, towards the annular inlet slit in the second circular electrical mobility selector.

Therefore the first purpose of the invention relates to a device comprising two circular electrical mobility selectors (SMEC) placed in series. In operation, the two SMECs are placed such that the annular inlet slit in the first is located above (or below) its annular outlet slit, whereas the annular inlet slit in the other is located below (or above) its second disk. Under these conditions, particles that enter the first circular electricity mobility selector are drawn towards its selection slit under the combined action of the laminar, centripetal and stable air flow circulating between the two disks, the electrical field imposed between the two disks, and the gravity field. The particles thus selected initially are recovered and introduced into the second circular electrical mobility selector and are drawn towards the second disk in this second selector under the combined action of the radial and laminar air flow set up between the two disks in this second selector, the electrical field imposed between the two disks, and the gravity field.

The second disk in the second selector may also be fitted with an annular selection slit with radius r'2 <r'1. Therefore during operation, the annular inlet slit in the second disk is located above or below its selection slit, depending on the case.

Means may be provided for varying the electrical fields set up in the two disks and for sampling the values corresponding to the particle selection. This thus gives numeric values which may be easily related to the electrical mobility and the particle relaxation time.

These two magnitudes are related to the geometric diameter of the particles, their state of charge and their density. Consequently, if one of these three magnitudes is known, or is assumed, the other two magnitudes can be determined. Similarly, the particle mass can be related to a simple combination of measured values for electrical fields corresponding to the particle selection.

According to one particular embodiment of the invention, the extraction slit in one (or both) electrical mobility selectors may be reduced to a central orifice. The selector with a central extraction orifice is easier to make than the device with an annular extraction slit, and has better performances with a shorter transit time in the particle extraction circuit. It can avoid sedimentation problems in this circuit.

Another purpose of the invention is a selector of charged particles in an aerosol comprising:
 a first and a second circular electrical mobility selector, each selector comprising:
  a first and second coaxial conducting disk, separate and parallel to each other,
  a central intake, this intake allowing a laminar, centripetal and stable air flow to circulate in the space between the disks,
  means of applying an electrical field between the two conducting disks,
 means of introducing particles in the aerosol to be examined, in parallel into the two selectors.

In this second device, there are two circular electricity mobility selectors "in parallel". This second device may be even more compact than the first. It operates on principles similar to those mentioned above for the first device. During operation, aerosol particles are inlet for each selector above either the first or second disk, and below the other disk. In both circular selectors, particles are entrained towards the extraction slit under the combined action of the laminar, centripetal air flow, the electrical field and the gravity field. In this case too, the values of the electrical field are simply related to the electrical mobility and the particle relaxation time. Preferably, in this second device, the second conducting disks in each selector are coincident, which makes the assembly more compact.

At least one of the selectors may include an annular extraction slit with radius r1.

If there is an annular extraction slit in both selectors, then during operation the aerosol particles are introduced above the annular extraction slit in one of the two circular electrical mobility selectors, and below the annular extraction slit for the other.

Another selector according to the invention operating, like the above, with a "parallel" configuration, comprises:
 first and second coaxial conducting disks separate and parallel to each other, each comprising a central intake to circulate a laminar, centripetal and stable air flow in the space between the two disks,
 means of applying an electrical field between the two disks,
 means of introducing aerosol particles between the first and second disks, starting from the periphery of the two disks.

This device is even simpler to make than the previous device. It operates on exactly the same principle. Particles to be analyzed are then inlet simultaneously to two conducting disks, but above one of the two disks and below the other disk. They are still moved under the combined action of the same forces (laminar and radial air flow, electrical field, gravity field)

Regardless of which device is used, either "in series" or "in parallel", the operating principle is much simpler than the operating principle of the device described for example in the Emets et al. article mentioned above. In the selector according to the invention, the action of gravity acts linearly with the electrical field, and implies simply an offset of the transfer function for one selector with respect to the other, without deforming this function. However in "DMA" type instruments with axial flow, the action of gravity, which does not act linearly with the electrical field, causes a complex deformation of the horizontal DMA transfer function. The consequence is that it becomes very difficult to interpret the results, which is not the case for a device according to the invention.

In all cases, means may be provided to vary the electrical field applied in the first, and/or the second circular electrical mobility selector(s), or between the two conducting disks in order to carry out a spectrometry.

Means may be provided for sampling the value(s) of the applied electrical field corresponding to the selection of a particle type, and other means may be provided to combine, add or and/or subtract sampled values. These values may be used with calculation means to calculate the electrical mobility of selected particles and/or their relaxation time, and/or their geometric diameter, and/or their mass, and/or their density.

A selector like that described above may also comprise means for varying one of the two air flow rates.

Furthermore, it may comprise means of detecting or collecting charged particles.

A spectrometer for charged particles according to the invention, may comprise a selector such as that described above.

The invention also relates to a device for measuring the particle size of an aerosol comprising a spectrometer as described above, and means for determining the particle size of the aerosol.

BRIEF DESCRIPTION OF THE FIGURES

In any case, the characteristics and advantages of the invention will be better understood after reading the following description. This description relates to embodiment examples given for explanation and in no way restrictive, referring to the drawings in the appendix in which.

DETAILED DESCRIPTION OF EMBODIMENTS OF THE INVENTION

A first embodiment of a selector according to the invention will be described with reference to FIG. 1. This figure shows two circular electrical mobility selectors 2, 4 located in series, particles selected by the first selector 2 being placed at the inlet to the second selector 4.

The first selector comprises two disks 6, 8, parallel and concentric, defining a selection zone 3 between them. The two disks are separated by a distance 2h. The upper disk 6 has an annular slit 14 with radius $r_1$ through which an aerosol is input at a flow $Q_a$. A central suction pipe 22 formed in the upper disk extracts a flow $Q_o$ from the selection zone 3. An annular opening 16 with radius $r_2$ ($r_2 < r_1$) is formed in the second disk 8. When the equipment is in operation, a flow $Q_a$ of selected particles passes through this slit 16. A flow $Q_o$ of an entrainment gas (usually filtered air) is introduced between the two disks at the periphery of space 3, by means not shown on FIG. 1. Due to the circular structure of the equipment, a laminar, stable and centripetal flow circulates between the two disks, with a flow $Q_o$ as far as suction tubing 22.

Means are provided to impose an electrical field $E^-$between the two disks 6, 8. In particular, the two disks may be conducting and each may be at a given potential, for example 0 for disk 6 and $U^-$for disk 8.

Selected particles may be directed to the second electrical mobility selector 4, by means of a box 26 such as a cylindrical box, and ducts 28, 34.

This second electrical mobility selector has elements similar to those in selector 2. In particular, two parallel and concentric disks 10, 12 separated by a distance 2h define a selection zone 5 between them. The lower disk 12 includes an annular slit 18 with a radius $r'_1$ through which aerosol particles selected by the first selector 2 are introduced into the second selector, at a flow $Q_a$. A central suction pipe or tubing 24 formed in the lower disk 12 extracts an air flow $Q'_o$ from the selection zone 5. An annular opening 20 with radius $r'_2$ ($r'_2$ <$r'_1$) is formed in the upper disk 10. When the equipment is in operation, a flow $Q_a$ of selected particles passes through this slit 20. A flow $Q_o$ of an entrainment gas (usually filtered air) is introduced between the two disks 10, 12 at the periphery of space 5, by means not shown on the figure. Due to the circular structure of the equipment, a laminar, stable and centripetal flow circulates between the two disks.

Means are provided to impose an electrical field $E^+$ between the two disks 10, 12. In particular, the two disks may be conducting and each may be at a given potential, for example 0 for disk 12 and $U^+$ for disk 10.

Selected particles may then be directed by a box 30 such as a cylindrical box and a duct 32, towards any type of device suitable for the envisaged application, for example towards a particle counting detector. This detector may work based on electrical or optical methods. In particular, it may be a light diffusion type of detector, in which the particles to be analyzed are entrained by the gaseous flow through a light beam produced by a light source. Each particle then diffuses a given quantity of light which is then analyzed by a light detector. Analysis means may also be provided to collect and process data. These means may include a conventional microcomputer programmed as a function of the envisaged application, in other words the type of characteristics to be calculated or represented (application examples are given later). Program instructions may be stored on conventional RAM or ROM.

Selected particles may also be directed towards an aerosol collector, for example a mechanical collector which may be connected to an electrometer, or an electrostatic collector that may be fitted with a nuclear detector for the analysis of radioactive aerosols. For example, this type of collector may be placed in box 30 in the second selector. A mechanical collector comprises a porous membrane on which particles are deposited and may subsequently be analyzed, for example by weighing.

In a variant of the invention, one of the two electrical mobility selectors may be fitted with a suction duct formed in the disk in which the annular extraction opening is located (disk 8 in the first selector, disk 10 in the second selector).

In FIG. 1, the first circular selector has an annular particle inlet slit 14 located above the annular selection slit 16. The reverse is true for the second circular selector 4. It is also possible to make a device in which the annular particle inlet slit in the first selector is located below the annular selection slit, whereas the annular inlet slit in the second circular selector is above its annular selection slit. In other words, the upstream and downstream circular selectors are indifferent and their position can be changed. The center line of the selectors (perpendicular to disks 6, 8, 10 and 12) may be kept vertical.

In the first selector 2, the movement of particles from inlet slit 14 towards selection slit 16 takes place under the combined action of:

- the radial and laminar air flow $Q_o$ existing between the two disks,
- the electrical field $E^-$, imposed between the two disks, this field inducing a particle drift speed $V_E^-$,
- the gravity field (acceleration g ) that induces a sedimentation speed $V_S$, which is superimposed on the drift speed $V_E^-$.

The particles thus selected initially are then transported towards the second selector, once again at flow$_a$; they are then introduced through the slit with radius $r'_1$. They are then entrained towards extraction slit 20 under the combined action of:

- the radial, laminar and centripetal air flow $Q'_o$ existing between the two disks 10, 12,
- the electrical field $E^+$ imposed between the two disks 10, 12, which induces a drift speed $V_E^+$.
- the gravity field (acceleration g) that induces a sedimentation speed $V_S$, which is superimposed on the drift speed $V_E^+$.

It can be demonstrated that the $E^-$ and $E^+$ fields that have to be set up in the two circular selectors in order to select a particle with electrical mobility Z and relaxation time τ, are given by the following equations:

$$E^- = \frac{Q_o}{\pi Z(r_1^2 - r_2^2)} - \frac{\tau g}{Z} \qquad (1)$$

$$E^+ = \frac{Q'_o}{\pi Z(r_1'^2 - r_2'^2)} - \frac{\tau g}{Z} \qquad (2)$$

Note that the action of the gravity field is only significant if the particle relaxation time is long.

If selector disks 6, 8, 10, 12 are increased to potentials OV, $U^-$, $U^+$, OV respectively in order to set up the $E^-$ and $E^+$ fields, relations (1) and (2) above become:

$$\frac{U^-}{2h} = \frac{Q_o}{\pi Z(r_1^2 - r_2^2)} - \frac{\tau g}{Z} \qquad (1')$$

$$\frac{U^+}{2h} = \frac{Q'_o}{\pi Z(r_1'^2 - r_2'^2)} - \frac{\tau g}{Z} \qquad (2')$$

Therefore, the electrical mobility of the particles and their relaxation time can be determined by making a simple measurement of the voltages or fields corresponding to the selection of a particle type and using relations (1), (1') and (2), (2') above.

If the electrical mobility is obtained, the geometric diameter of the particles can also be obtained if the number of electrical charges carried by a particle is known.

The electrical mobility and the relaxation time can easily be obtained by combination (addition and subtraction) of the fields or voltages given by the following equations:

$$U^- + U^+ = \frac{4HQ_o}{\pi Z(r_1^2 - r_2^2)} \qquad (3)$$

$$U^+ - U^- = \frac{4h\tau g}{Z} \qquad (4)$$

(equations (3) and (4) are valid if $Q_o = Q'_o$, $r_1 = r'_1$ and $r_2 = r'_2$; if this is not the case, simply input an appropriate weighting factor in order to deduce the equivalent relations, firstly in $1/Z$ and secondly in $\tau/Z$).

Furthermore, the relaxation times and the electrical mobility are related to the geometric diameter $d_p$, to the density $\rho_p$ and to the number of electrical charges n of the particles by the following equations:

$$\tau = \frac{d_p^2 \rho_p C(d_p)}{18\mu} \qquad (5)$$

$$Z = \frac{neC(d_p)}{3\pi \mu d_p} \qquad (6)$$

where $\mu$ is the viscosity of the carrier gas, e is the elementary electrical charge and $C(d_p)$ is the Cunningham's correction factor ($C(d) = 1 + (ae/d) + (be/d)\exp(-cd/e)$, where a, b and c are constants and e represents the average free path of gas molecules).

These equations mean that the state of charges and particle diameters can be determined starting from the electrical mobility and the relaxation time, provided that an assumption is made about the particle density $\rho_p$. In fact in practice, it is usually not very difficult to make an assumption about the density.

For spherical particles, relation (4) may be put in the following form:

$$U^+ - U^- = 4h \, g \, M/ne \qquad (7)$$

where m is the particle mass. Therefore the difference in the voltage (or a linear combination of voltages) applied to the two selectors can give the mass measurement directly, which is equivalent to making an "electrodynamic balance with aerosol particles" operating in line, particularly for aerosols for which the number n of electrical charges per particle is known or can be estimated.

The device according to the invention has been presented with a second selector equipped with an outlet slit. But it is possible to use a solid disk instead of the upper disk 10 on the second selector equipped with an extraction slit. In this case, particles selected by the first selector are deposited on this disk in the second device. The deposit made at distance r from the center line of this second device corresponds; to particles with mobility Z and relaxation time $\tau$ given by relations (1) and (2), by replacing $r'_2$ by r. The deposit obtained may be analyzed later. This method may also be used to produce a standard deposit.

A variant of the first embodiment will now be described in relation to FIG. 2. The only difference between the device shown and FIG. 1 is the annular extraction slits in each of the two circular selectors, which are actually reduced to a central extraction orifice 36, 38. The other elements are identical and consequently have the same numeric references.

The device works in the same way as is described above in relation to FIG. 1, and has the same advantages although the central extraction orifice is a singular point in the air flow since it is the point at which laminar flow ceases. The equations mentioned above are also applicable when $r_2 = r'_2 = 0$. The additional advantage of this configuration is as follows. In the embodiment shown in FIG. 1, particle extraction through an annular slit requires that a box 26, 30, for example a cylindrical box, is implemented between the extraction slit and the extraction duct 28, 32. Particle transport in system circuits may then cause losses by diffusion in the vicinity of the walls, and losses by sedimentation, particularly in boxes 26, 30. Furthermore, the transit time in boxes, which may be long, is not the same for all particles and consequently there is a certain amount of dispersion through the device which may be a nuisance an some applications. On the other hand, the device with central extraction ensures that there are less particle losses after they exit from the selector, and shortens the transit time in extraction circuits.

The diameter $\phi$ of orifice 36, 38 is preferably chosen to provide good particle selectivity (the selectivity is low if the diameter is high), and also to avoid disturbing the fluid flow that passes through it (a "jet" phenomenon occurs at this orifice if the diameter is small).

Two other variants may also be made: firstly, when one of the two selectors has a central extraction orifice and the other has an annular extraction orifice, arid vice versa.

Obviously, as already mentioned above, if disk 10 in the second selector is solid instead of having a selection orifice or slit, the outlet or extraction slit in the first selector can be reduced to an orifice 36.

Another embodiment of the invention will now be described in relation to FIGS. 3 and 4 which show two variants. This embodiment corresponds to the implementation of two circular selectors 'in parallel'.

Figure 3:
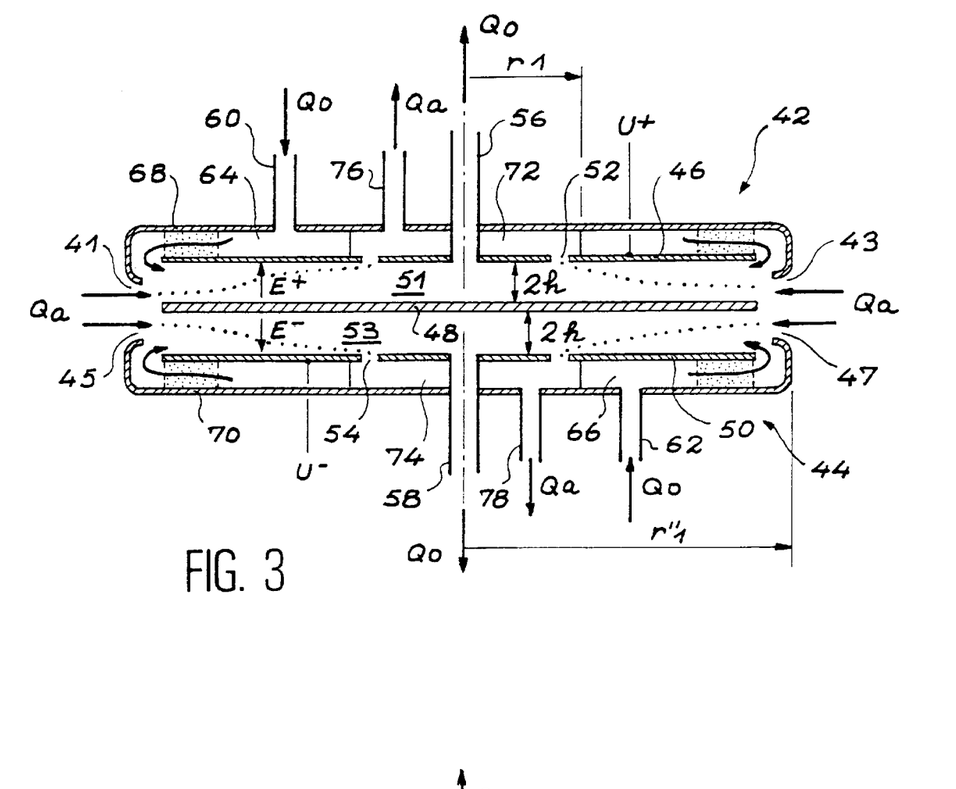
FIGS. 3 and 4 represent two variants of a second embodiment of a device according to the invention.

Thus on FIG. 3, each selector 42, 44 has two parallel and concentric disks 46, 48 and 50, 48. In fact on FIG. 3, the two central disks have been combined into a single disk 48. The two pairs of disks 46, 48 and 50, 48 define two selection areas 51, 53. The two outer disks 46, 50 (which can still be called the upper disk and lower disk) each have an annular particle extraction slit 52, 54, at radius $r_1$ about the center line of the disks. Similarly, the two outside disks 46, 50 each have a central suction pipe or tube 56, 58 used to extract air from the selection zone 51, 53 at a flow $Q_o$. Between each pair of disks, there are means not shown on the figure of adding an entrainment gas (usually filtered air) at flow $Q_o$. In the embodiment shown on FIG. 3, the entrainment gas is introduced through a tubing 60, 62 into a space 64, 66 located above and below the outside disks 46, 50 respectively between these disks and a cover 68, 70. The folded down edges of the covers then force the air towards the selection zone 51, 53. Suction through tubings 56, 58 guarantees centripetal, laminar and stable flow. The aerosol containing the particles to be selected may be introduced in each of the two selectors through a peripheral zone 41, 43, 45, 47 on the equipment, at a flow Qa. Particles are selected through slits, 52, 54 and are then extracted by extraction means composed of chambers 72, 74 formed between disks 46, 50 and covers 68, 70, and through extraction tubing 76, 78.

In this device, the "aerosols" inlet to one of the selectors 42 is placed lower than its extraction slit 52, whereas the "aerosols" inlet in the other selector 44 is higher than its extraction slit 54. Particles to be analyzed are introduced in the same position in both selectors simultaneously, at a distance $r''_1$, from the center line. For example, the center line of the equipment (perpendicular to disks 46, 48, 50) may be kept vertical.

Means may be provided for applying different potentials to the various disks 46, 48, 50, in order to set up an electrical field E in each of the two selectors. A configuration respecting the symmetry of the equipment consists of putting the intermediate plate 48 at a zero potential, and putting plates 46, 50 at potentials $U^+$ and $U^-$ respectively. In the configuration on FIG. 3, it is possible to work on particles with the same sign in selection zones 51 and 53.

Particle movements in zones 51 and 53 take place under the combined action of:

the radial and laminar air flow at flow $Q_o$ the electrical fields $E^+$ and $E^-$ imposed between the disks, which induce drift speeds of $V_E^+$ and $V_E^-$, the gravity field which induces a sedimentation speed $V_S$. which is superimposed on the speed $V_E^-$ in the lower selector 44, and which opposes the drift speed $V_E^+$ in the upper selector 42.

In the same way as in the first embodiment (selectors placed in series), it is possible to demonstrate that the electrical selection fields $E^+$, $E^-$ in the two selectors for a particle with mobility Z and relaxation time τ are as follows,:

$$E^- = \frac{Q_o}{\pi Z(r_1''^2 - r_1^2)} - \frac{\tau g}{Z} \quad (8)$$

$$E^+ = \frac{Q_o}{\pi Z(r_1''^2 - r_1^2)} - \frac{\tau g}{Z} \quad (9)$$

These relations can be used to deduce the electrical mobility and the relaxation time of the selected particles. Here again, and in the same way as has already been described above, the density, diameter, mass and number of electrical charges per particle can be determined.

Figure 4:
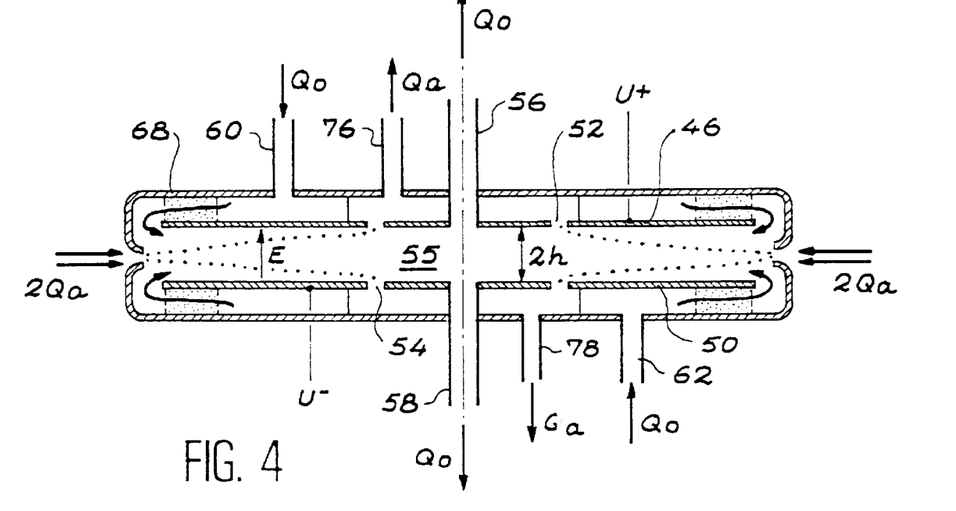

A variant to this second embodiment is illustrated on FIG. 4. This variant is different from that on FIG. 3. in that the central plate 48 is deleted; this plate was initially used as a second circular disk for each of the selectors 42, 44. The operating mode of this variant is exactly the same as the mode described in relation to FIG. 3. It is advantageous if the absolute values of the $U^+$ and $U^-$ voltages applied to disks 46, 50 are identical but of opposite signs, for example positive on the upper part and negative on the lower part, in order to provide a potential of about zero along the axis of symmetry of the device, which corresponds approximately to the zone in which particles are introduced.

If particles carry positive and negative charges, particles selected through slit 52 will have a negative charge, whereas those selected through slit 54 will have a positive charge.

Particle movements in zone 55 take place under the combined action of:

the radial and laminar air flow equal to $2Q_o$, the electrical field E imposed between the disks and which induces a drift speed $V_E$, the direction of which depends on the sign of the particle charge, the gravity field, which induces a sedimentation speed $V_S$ which is superimposed on the speed $V_E$ for particles selected through slit 54 and which opposes the drift speed $V_E$ for particles selected through slit 52.

As for the first embodiment, and the first variant of the second embodiment, it can be shown that for the electrical selection fields $E^-$ and $E^+$ necessary to extract a particle with mobility Z and relaxation time τ0 through slits 54 and 52 are given by equations (8) and (9).

In the case in the example described above, and in the case of the first embodiment, the selected particles may be directed towards any appropriate device, for example a particle collection device, or a detection device for counting particles. Similarly, data analysis means such as a specially programmed microcomputer may also be provided.

Finally, the two variants described above in relation to FIGS. 3 and 4 may operate with solid disks on which the deposits are made, rather than with disks 46, 50 in which outlet slits are formed. At any distance r, the properties of these deposits are governed by equations (8) and (9), replacing $r_1$ by r.

Regardless of the envisaged embodiment, means may be provided to vary the electrical field in either of the selectors, and/or the scavenging gas flow(s) $Q_o$, $Q'_o$. When this type of device is coupled to a particle detector to count the particles, then a particle spectrometer can be used to determine spectrum of the particle charges and sizes, if for example the density of the particles is known.

We have already seen that it is possible to make a device to determine the following, using the electrical mobility Z and the relaxation time τ:

the mass of the selected particles, particularly if they are spherical, with diameters equal to or greater than 0.1 μm (the mass of smaller sizes is very low and gravitation forces no longer play any significant role in the device), the density of the particles, once again for spherical particles with diameters equal to 0.1 μm or more.

Similarly, using the above equations for particles with approximately known densities, it is possible to calculate a pair of voltages or electrical fields to be applied, in order to select particles diameter $d_p$ and with a fixed charge n. Conversely, the voltages data or the electrical field data, and the flow data $Q_o$ determine the diameter $d_p$ and the state of charge n of the particles which Will be selected.

Consequently, the device is not only a selector, but also a generator of particles with fixed ($d_p$, n) characteristics or with fixed (z, τ) characteristics.

Furthermore, if particles with a number of fixed elementary charges are available, it is sufficient to determine the pairs of voltage or electrical fields to be applied to the equipment in order to select particles with a given diameter $d_p$.

Figure 1:
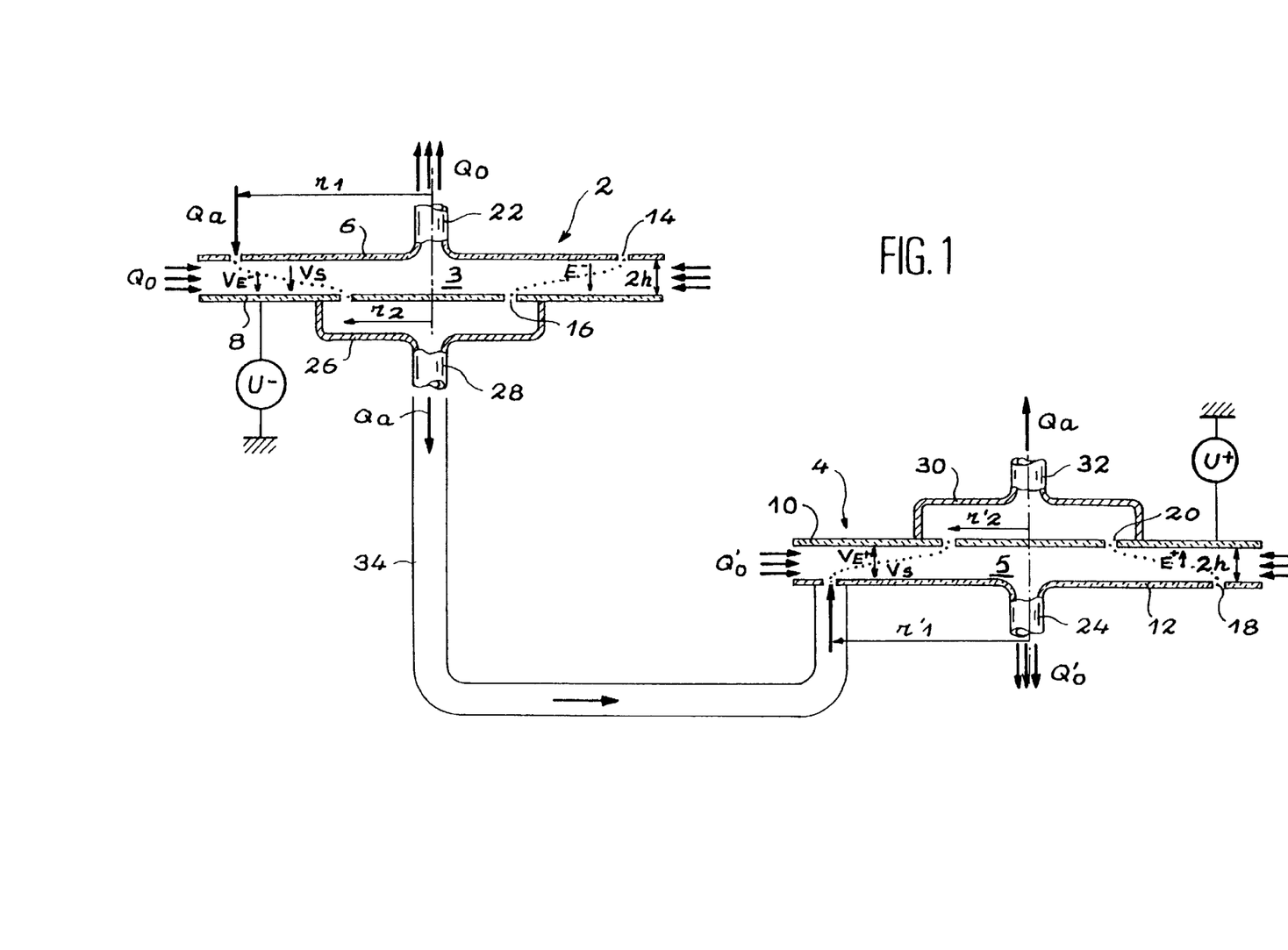
FIGS. 1 and 2 represent two variants of a first embodiment of a device according to the invention.
Figure 2:
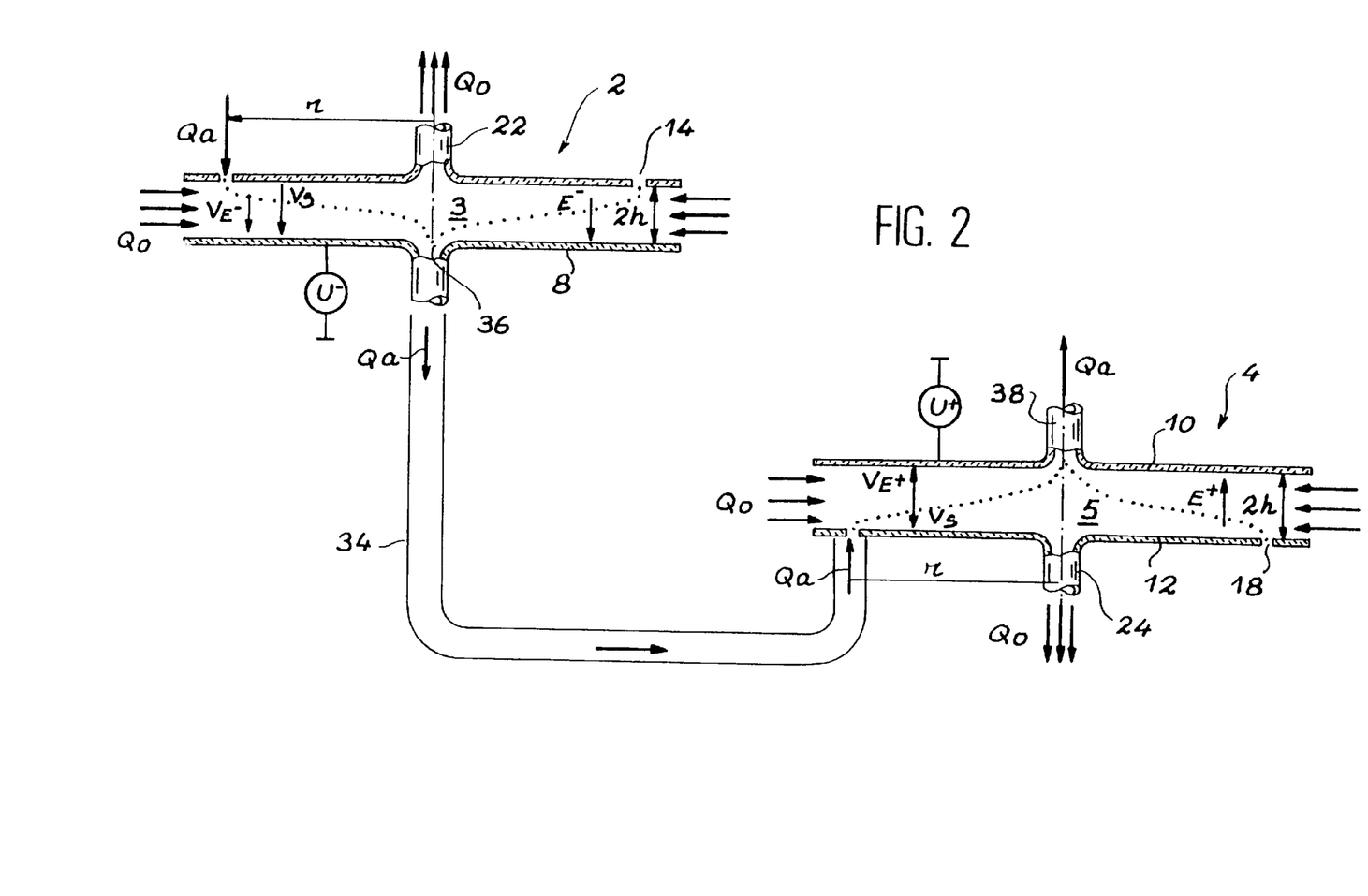

Conversely, by measuring the concentration of particles outlet from the selector (particularly for a selector "in series", in other words of the type shown in FIGS. 1 and 2) for different pairs of voltages or electrical fields applied to the device, it is possible to determine the particle size of the aerosol, in other words the aerosol size distribution. In order to do this, it is necessary to take account of the state of charge of the aerosol to be analyzed (which as we have seen is known), the selector transfer function and its various parameters (geometric parameter and flow parameter). This operation may be carried out for different numbers of fixed elementary charges, thus characterizing the size and charge of the aerosol.

The main lines of the mathematical processing to determine the unknown size distribution function of the sampled aerosol may be summarized as follows. For a pair of voltages V1, V2 applied to two selectors placed in series, the response R(V1,V2) of a detector placed downstream from the second selector is given by the following relation:

$$R(V_1, V_2) = \sum_{n=0}^{\infty} [Q_a F_n(d_p) N(d_p) P(d_p, n, V_1, V_2) dd_p]$$

where $Q_a$ represents the aerosol injection flow, $F_n(d_p)$ represents the fraction, assumed to be known, of particles of diameter $d_p$ carrying n elementary charges, $P(d_p, n, V_1, V_2)$ is the transfer function for the two selectors in series, i.e. the probability of selecting particles of diameter $d_p$ carrying n charges when the pair $V_1$, $V_2$ is applied, and finally $N(d_p)dd_p$ is the unknown distribution function. If several pairs $V_1$ and $V_2$ are applied, different responses $R(V_1, V_2)$ are obtained, together with a system of equations that can be used to determine the $N(d_p)dd_p$ function by conventional mathematical inversion techniques.

In the case of a selector operating "in parallel" (of the type shown on FIGS. 3 and 4), for each value of the voltage set up between the different disks, particles with determined values for the electrical mobility and the relaxation time are chosen in the lower and upper parts respectively. Thus, by measuring the concentrations of particles outlet from the lower and upper parts of the device respectively for each voltage, it is possible to determine the particle size of the aerosol, once again taking account of the state of charge of the aerosol, transfer functions and the various equipment parameters.

Finally, for a fixed particle diameter dp, if the charge law is unknown, it is possible to determine the voltages or electrical fields that have to be applied to select different elementary charges, regardless of the considered embodiment. The concentration of particles outlet from the selector is then measured for the voltages or electrical fields thus determined. Therefore for a fixed diameter, the particle distribution is determined as a function of their charge, i.e. their charge distribution. If this is done for different fixed diameters $d_p$, the particles can be characterized in charge and in diameter.

Figure 5:
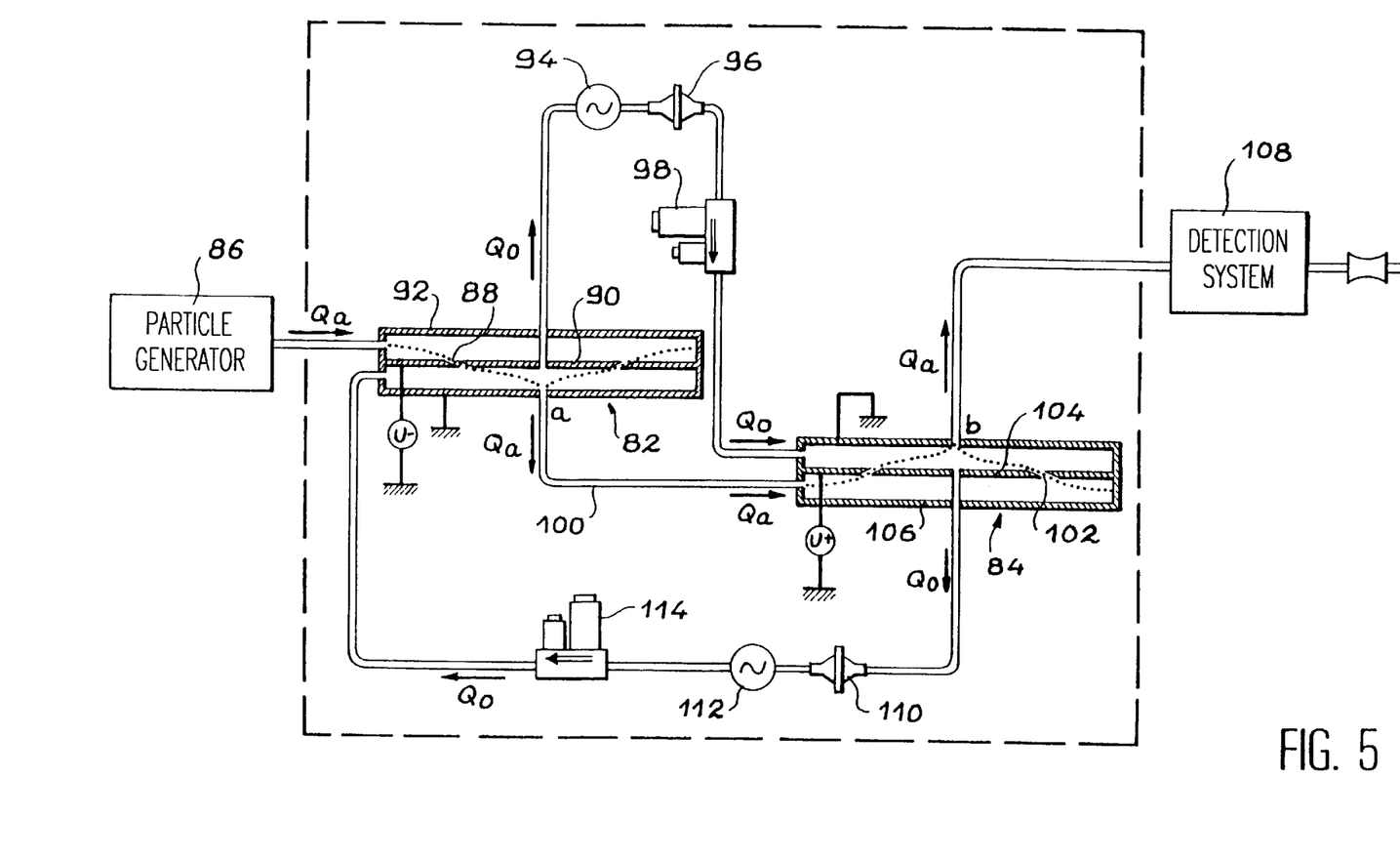
FIG. 5 illustrates an example of an embodiment of a device according to the invention.

An example embodiment of a device according to the invention will now be described in relation to FIG. 5. The chosen device is of the "in series" type with a central extraction orifice, in other words of the type shown in FIG. 2. The two circular selectors thus used are shown as references 82 and 84 respectively. Particle generation means 86 firstly put the particles to be characterized in suspension (for example, these means may include a powder or liquid spraying system using pneumatic methods), and secondly apply a given state of charge to the sprayed particles, so that the aerosol obtained can be assigned a given statistical charge distribution law as a function of the diameter. A flow $Q_a$ of a gas sample containing the particles is then continuously introduced through the annular slit 88 in the upper disk 90 of selector 82. For example, these particles may be introduced through an intermediate stage defined by disk 90 and another disk 92 located above this disk 90. The laminar, centripetal and stable flow $Q_o$ is set up in selector 82 by a circuit comprising a pump 94, a filter 96 and a flow regulator 98. Consequently, this gas circulation circuit does not close on the inlet of selector 82, but on the inlet of selector 84, the intake circuit for the second selector being connected to the inlet of selector 82. The particles selected by the first selector 82 are transferred through a duct 100 towards selector 84. They pass through the annular slit 102 in the lower disk 104. For example, these particles may be introduced through an intermediate stage defined by the disk 104 and another disk 106 located below it. The laminar, centripetal and stable gas flow $Q_o$ is created by the circuit comprising pump 112, filter 110 and the flow regulator 114. Particles selected by the selector outlet orifice pass towards detection system 108. Since the initial particles have a given state of charge, particles counted by detector 108 are particles with a diameter determined by the voltages or electrical fields, and by the geometric and flow characteristics of equipment 82, 84.

In the case of a selector operating "in series" (such as that described with reference to FIG. 2) the following experiment was carried out. An electrical field E⁻ was applied to the first selector to select spherical particles of "Latex" polystyrene with a perfectly known diameter. Furthermore, the electrical field E⁺ necessary to extract these particles outlet from the first selector, from the second selector, was determined. The voltage differences U⁺ and U⁻ corresponding to the E⁺ and E⁻ fields must satisfy the relation (7) above.

Figure 6:
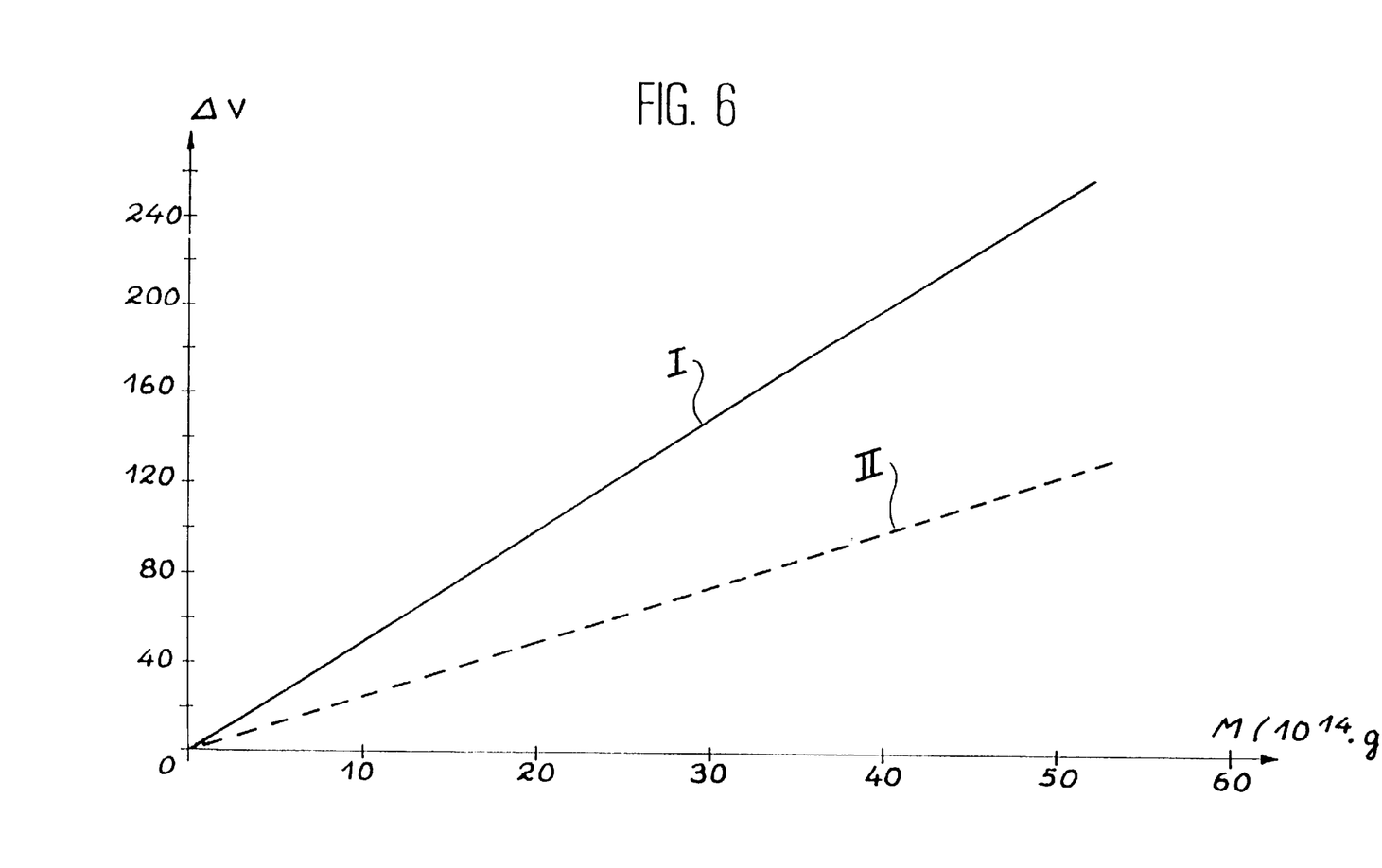
FIG. 6 illustrates a comparison between experimental and theoretical values measured with, and calculated for, a device according to the invention.

FIG. 6 shows the comparison between the values of the voltage differences given by relation (7), and experimentally determined values, for particles with diameters of between 0.107 μm and 0.966, and therefore with masses between $5.10^{-16}$ grams and about $5.10^{-13}$ grams. The straight lines I and II are applicable for states of charge n=1 and n=2 respectively, the experimental values then being shown by squares and black dots respectively. Very good agreement is found between theoretical predictions and experience, with an uncertainty on masses of less than 5% for the largest particles.

Therefore the device according to the invention is a new type of differential electrical mobility analyzer which, by its principle, can determine the particle size, particularly for supermicronic particles (particle size greater than or equal to 1 μm, and particularly between 2 and 5 μm). Conventional, known and marketed systems are usually limited to particles smaller than 1 μm. This type of equipment can only provide one item of information, namely the electrical mobility. However, supermicronic particles may carry large multiple charges, and deconvolution of the signal then becomes impossible. Therefore, it is necessary to have information about the number n of charges carried by the selected particles, which can be done by the system according to the invention, making use of these two items of information originating from a double selection carried out in series or in parallel.

We claim:

1. A spectrometer of charged particles in an atmosphere to be examined, comprising a selector of charged particles, said selector comprising:

first and a second circular electrical mobility selectors, each circular electrical mobility selector comprising, first and second coaxial disks, separate and parallel to each other, with an annular inlet slit of radius $r_1$ being formed in the first disk of the first circular electrical mobility selector and an annular inlet slit of radius $r'_1$ being formed in the first disk of the second circular electrical mobility selector, a central intake allowing a laminar, centripetal and stable air flow to circulate in the space between the two disks, and means for applying an electrical field between the two disks; and means for directing particles selected by an annular selection slit with radius $r_2$ that is less than radius $r_1$ formed in the second disk in the first circular electrical mobility selector towards the annular inlet slit in the first disk of the second circular electrical mobility selector; and means for varying the electrical field applied in the first and/or the second circular electrical mobility selector.

2. A spectrometer according to claim 1, further comprising means of sampling the value of the applied electrical field.

3. The spectrometer according to claim 2, further comprising means of adding and/or subtracting sampled values of electrical fields.

4. The apparatus according to any one of claims 1 to 8, further comprising means of calculating the electrical mobility of the selected particles, or their relaxation time and/or their geometric diameter or their mass or their density.

5. The spectrometer according to claim 2, further comprising means for combining, adding or subtracting the sampled values.

6. The spectrometer according to claim 5, further comprising means for calculating the electrical mobility of the selected particles, or their relaxation time or their geometric diameter or their mass or their density or their charge.

7. The spectrometer according to claim 1, further comprising means for detecting charged particles.

8. A device for measuring the particle size of an aerosol comprising a spectrometer according to claim 1 and means for determining the particle size of the aerosol.

9. A process for selecting charged particles using a selector, said selector being a selector of charged particles in an atmosphere to be examined, comprising:

first and second circular electrical mobility selectors, each circular electrical mobility selector comprising, first and second coaxial disks, separate and parallel to each other, with an annular inlet slit of radius $r_1$ being formed in the first disk of the first circular electrical mobility selector and an annular inlet slit of radius $r'_1$ being formed in the first disk of the second circular electrical mobility selector, a central intake allowing a laminar, centripetal and stable air flow to circulate in the space between the two disks, means for applying an electrical field between the two disks; and means for directing particles selected by an annular selection slit with radius $r_2$ which is less than radius $r_1$ formed in the second disk in the first circular electrical mobility selector towards the annular inlet slit in the first disk of the second circular electrical mobility selector, wherein the second disk of the second circular electrical mobility selector has an annular selection slit with radius $r'_2$, wherein $r'_2$ is less than $r'_1$, and wherein the first circular electrical mobility selector has its annular inlet slit located above its selection slit and the second circular electrical mobility selector has its annular inlet slit located below its second disk, said process comprising:

introducing charged particles into said first circular electrical mobility selector, and, in each circular electrical mobility selector, the further steps of, circulating a laminar, centripetal and stable air flow in the space between the two disks, applying an electrical field between the two disks;

said process further comprising, directing particles selected by said annular selection slit towards said annular inlet slit in the second circular electrical mobility selector.

10. A method of using a selector, said selector being a selector of charged particles in an atmosphere to be examined, comprising:

first and second circular electrical mobility selectors, each circular electrical mobility selector comprising, first and second coaxial disks, separate and parallel to each other, with an annular inlet slit of radius $r_1$ being formed in the first disk of the first circular electrical mobility selector and an annular inlet slit of radius $r'_1$ being formed in the first disk of the second circular electrical mobility selector, a central intake allowing a laminar, centripetal and stable air flow to circulate in the space between the two disks, means for applying an electrical field between the two disks; and means for directing particles selected by an annular selection slit with radius $r_2$ which is less than radius $r_1$ formed in the second disk in the first circular electrical mobility selector towards the annular inlet slit in the first disk of the second circular electrical mobility selector, wherein the second disk of the second circular electrical mobility selector has an annular selection slit with radius $r'_2$, wherein $r'_2$ is less than $r'_1$, and wherein the first circular electrical mobility selector has its annular inlet slit located above its selection slit and the second circular electrical mobility selector has its annular inlet slit located below its second disk, said method comprising:

introducing charged particles into the first circular electrical mobility selector, and, in each circular electrical mobility selector, the further steps of, circulating a laminar, centripetal and stable air flow in the space between the two disks, applying an electrical field between the two disks;

said method further comprising, directing particles selected by said annular selection slit towards said annular inlet slit in the second circular electrical mobility selector.

* * * * *